US012252726B2

(12) United States Patent
Adsul et al.

(10) Patent No.: US 12,252,726 B2
(45) Date of Patent: Mar. 18, 2025

(54) PROCESS FOR SIMULTANEOUS PRODUCTION OF CITRIC ACID AND CELLULOLYTIC ENZYMES

(71) Applicants: INDIAN OIL CORPORATION LIMITED, Mumbai (IN); DEPARTMENT OF BIOTECHNOLOGY, New Delhi (IN)

(72) Inventors: Mukund Adsul, Faridabad (IN); Simranjeet Kaur Sandhu, Faridabad (IN); Reeta Rani Singhania, Faridabad (IN); Anshu Shankar Mathur, Faridabad (IN); Ravi Prakash Gupta, Faridabad (IN); Deepak Kumar Tuli, Faridabad (IN); Suresh Kumar Puri, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 806 days.

(21) Appl. No.: 17/390,956

(22) Filed: Jul. 31, 2021

(65) Prior Publication Data
US 2021/0355511 A1 Nov. 18, 2021

Related U.S. Application Data

(63) Continuation-in-part of application No. 16/698,666, filed on Nov. 27, 2019, now Pat. No. 11,149,261.

(30) Foreign Application Priority Data

Nov. 28, 2018 (IN) .............................. 201821044919
Jul. 14, 2021 (IN) .............................. 202123031729

(51) Int. Cl.
*C12P 7/48* (2006.01)
*C12N 1/20* (2006.01)
(Continued)

(52) U.S. Cl.
CPC .................. *C12P 7/48* (2013.01); *C12N 1/20* (2013.01); *C12P 21/02* (2013.01); *C12P 2203/00* (2013.01); *C12R 2001/80* (2021.05)

(58) Field of Classification Search
CPC .......... C12N 1/20; C12N 1/14; C12N 9/2437; C12N 1/145; C12P 21/02; C12P 7/48; C12P 2203/00; C12R 2001/80
See application file for complete search history.

(56) References Cited

U.S. PATENT DOCUMENTS 4,931,352 A 6/1990 Fromtling
8,043,844 B2 10/2011 Sabatier et al.
(Continued)

FOREIGN PATENT DOCUMENTS

CN 103045484 B 12/2014
EP 3628751 A1 4/2020
(Continued)

OTHER PUBLICATIONS

Max et al. Biotechnological Production of Citric Acid. Brazilian Journal of Microbiology (2010), 41, 862-875. (Year: 2010).*
(Continued)

*Primary Examiner* — Sean C. Barron
(74) *Attorney, Agent, or Firm* — Maschoff Brennan

(57) ABSTRACT

The present invention relates to a process for simultaneous production of citric acid and cellulolytic enzymes. The batch process comprising (i) adding slurry of a pre-treated lignocellulosic biomass or cellulose in a fermentation media; (ii) inoculating 10% (v/v) active liquid seed culture of *Penicillium funiculosum* MRJ-16 in the fermentation media of step (i); (iii) subjecting the culture of step (ii) to fermentation in an aerated fermenter at a temperature of 28-33° C. for a duration of 96 hours; and (iv) collecting enzyme broth after fermentation of step (iii) to obtain citric acid and cellulolytic
(Continued)

enzymes. The batch and fed-batch process of the present invention results in high titer production of citric acid and cellulolytic enzymes in a single step and using single microbial strain.

12 Claims, 1 Drawing Sheet

(51) Int. Cl.
   *C12P 21/02* (2006.01)
   *C12R 1/80* (2006.01)

(56) References Cited

U.S. PATENT DOCUMENTS

| | | | |
|---|---|---|---|
| 8,956,846 | B2 | 2/2015 | Ben Chaabane et al. |
| 9,249,402 | B2 | 2/2016 | Ben Chaabane et al. |
| 10,526,593 | B2 | 1/2020 | Yazdani et al. |
| 2011/0262997 | A1 | 10/2011 | Smith et al. |
| 2014/0045227 | A1 | 2/2014 | Rarbach et al. |
| 2014/0363846 | A1 | 12/2014 | Edwards et al. |
| 2020/0102621 | A1 | 4/2020 | Adsul |

FOREIGN PATENT DOCUMENTS

| | | |
|---|---|---|
| RU | 2261910 C2 | 10/2005 |
| WO | 2010/076552 A1 | 7/2010 |
| WO | 2011/133111 A1 | 10/2011 |
| WO | 2017/174378 A1 | 10/2017 |
| WO | 2017/177289 A1 | 10/2017 |

OTHER PUBLICATIONS

Visagie et al. Identification and nomenclature of the genus Penicillium. Studies in Mycology (2014), 78, 343-371. (Year: 2014).*

Ghose, T.K. "Measurement of cellulase activities" Pure and Applied Chemistry, vol. 59, No. 2, pp. 257-268 (1987).

Smith, PK et al., "Measurement of protein using bicinchoninic acid" Analytical Biochemistry, vol. 150, No. 1, pp. 76-85 (1985).

Ahmed, S. et al., "Production and Purification of Cellulosedegrading Enzymes From a Filamentous Fungus Trichoderma Harzianum," Pakistan Journal of Botany, vol. 41, No. 3, pp. 1411-1419 (Jun. 2009).

Bansal, N. et al., "Production of cellulases from Aspergillus niger NS-2 in solid state fermentation on agricultural and kitchen waste residues," Waste Management, vol. 32, Issue 7, pp. 1341-1346 (Apr. 12, 2012).

Brijwani, K. and Vadlani, P. V. , "Cellulolytic Enzymes Production via Solid-State Fermentation: Effect of Pretreatment Methods on Physicochemical Characteristics of Substrate," Enzyme Research, vol. 2011, Article ID 860134, 10 pages (Jun. 2011).

Fawzi, E. M. "Production and Purification of β-Glucosidase and Protease by Fusarium proliferatum NRRL 26517 Grown on Ficus nitida Wastes," Annals of Microbiology, vol. 53, Issue 4, pp. 463-476 (2003).

Ogunmolu et al. Comparitive insights into the saccharification potentials of a relatively unexplored but robust Penicillium funiculosum glycoside hydrolase 7 cellobiohydrolase. Biotechnol Biofuels (Mar. 20, 2017) (10(71).

* cited by examiner

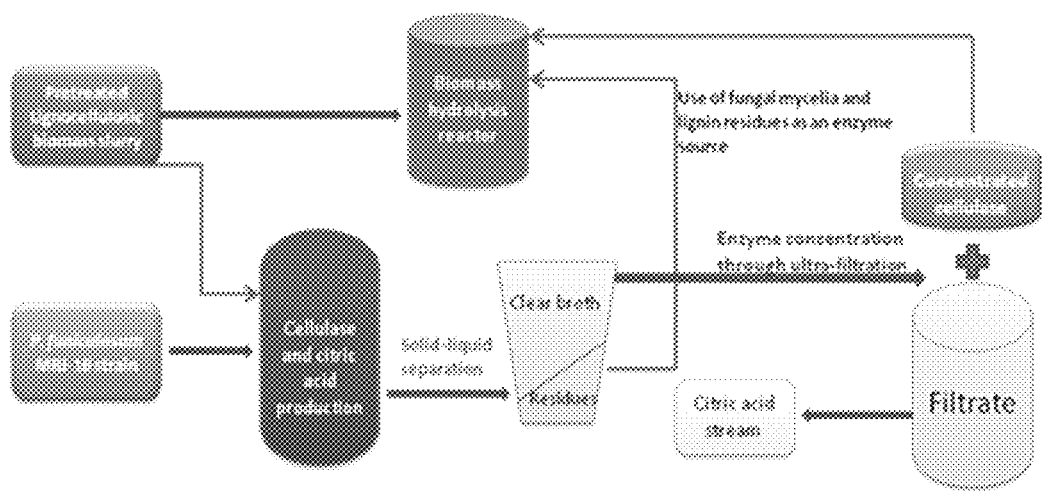

PROCESS FOR SIMULTANEOUS PRODUCTION OF CITRIC ACID AND CELLULOLYTIC ENZYMES

CROSS-REFERENCE TO RELATED APPLICATIONS

The present patent application is a patent of addition of the main Indian Patent Application No. 201821044919 of Filing date Nov. 28, 2018, and Publication date Jun. 5, 2020. The present application comprises an improvement or a modification of the invention claimed in the specification of the main patent applied for in the Indian Patent Application No. 201821044919.

FIELD OF THE INVENTION

The present invention relates to a process for simultaneous production of high titer citric acid and cellulolytic enzymes. More particularly, the present invention provides a process for simultaneous production of high titer citric acid and cellulolytic enzymes from a carbon source such as cellulose or lignocellulosic material in a single step and using single microbial strain. The present invention also relates to a fed batch process for production of citric acid and cellulolytic enzymes.

BACKGROUND OF THE INVENTION

Lignocellulosic biomass is an abundant and sustainable source of biopolymer for the production of fuels and chemicals. Cellulose and hemicelluloses are the polysaccharides present in this biopolymer and could be utilized for production of commodity chemicals. Cellulolytic and hemicellulolytic enzymes play an important role in the environmentally friendly conversion of these polysaccharides into their respective monomeric sugars. No doubt, that there is a significant market for hemicellulolytic and cellulolytic enzymes, however the cost of these enzymes is a major hurdle for the cost-competitive production of fuels and chemicals from cellulosic biomass. Till date, there is no viable technology in India which can produce indigenous cellulases enzyme for biomass hydrolysis in a cost-effective manner. Lack of hyper cellulolytic microorganisms, less enzyme titer, and high cost of growth media constituents are major limiting factors, which in turn makes its application processes quite expensive. Therefore, the reduction of overall enzyme production cost and the development of industrially viable strain are the major goals of enzyme manufacturing industries. To economize the process, a high titer of cellulolytic and hemicellulolytic enzymes, efficiency of enzyme cocktail for biomass hydrolysis, time required for enzyme production, and use of byproduct generated and are an important area to focus on.

Further, there are numerous methods which are known to reduce the cost of enzymes and one of them is the use of cheaper carbon as well as an inducer for enzyme production. Cheaper carbon sources such as agricultural residues (pretreated or untreated) could be sued for enzyme production. Agricultural residues such as rice straw, wheat straw, sugarcane bagasse, etc. could not be used directly, so a pretreatment process is employed before their use. Pretreatment of lignocellulosic biomass can involve multi-steps like washing, soaking, chemical, high temperature, steam explosion, etc. The most commonly used acid pretreatment of lignocellulosic biomass aimed to increase the surface area of cellulose by hydrolyzing a major fraction of hemicelluloses and a small fraction of cellulose so that enzymes easily access the cellulose and release glucose. Acid pretreatment hydrolyzes the hemicellulose fraction to release xylose, glucose, mannose, and arabinose, and depending upon the severity of treatment these sugars get converted into toxic substances such as hydroxyl methyl furfurals, formic acid, acetic acid, and furfurals. The presence of these inhibitors negatively affects the growth of some microorganisms and enzyme action.

Enzymatic breakdown of cellulose and hemicelluloses exposes required various cellulases, hemicellulases, and β-glucosidase enzymes. These enzymes are produced industrially by fungi belonging to genera *Trichoderma, Aspergillus*, and *Penicillium* sp. by submerged fermentation in either continuous or batch mode. For industrial purposes, these fungal strains are mutated to improve its properties such as high enzyme yield, high specific activity, minimum chemical requirement, and versatility of enzymes. Further, citric acid is an important organic acid and extensively used in the food industries. It has large number of applications in the pharmaceutical and cosmetics industries. In food industries, it is used as a stabilizer, preservative, antioxidant and acidulant, etc.

U.S. Pat. No. 9,249,402B2 describes the use of hemicellulosic hydrolysate, a soluble sugar, obtained from acid pretreated lignocellulosic material for enzyme production in a reactor using fungal strain *Trichoderma reesei*. This soluble sugar is used along with some inducer such as lactose, cellobiose, etc. to induce cellulases. The document did not use pretreated biomass directly but used acid hydrolyzed sugar for the growth of fungus and cellulase production along with other inducers. Separation of hydrolysate from acid pretreated lignocellulosic biomass is an additional cost-consuming step and also the used pure sugars as inducers as well as a carbon substrate for fungal growth. Instead of only soluble acid hydrolysate and pure inducer sugars, direct use of pretreated biomass as a carbon substrate as well as inducer will be more economical for large scale cellulase production.

US20140045227A1 describes the use of pretreated lignocellulosic biomass for cellulase enzyme production and their use for enhanced hydrolysis of the same pretreated biomass. The process used fungal strain *Trichoderma reesei*. However, the document does not mention the amount of protein or enzyme produced which may have affected because of the direct use of pretreated biomass containing inhibitors. Further, the document failed to describe the other valuable products/byproducts produced during the enzyme production.

US 20110262997A1 describes the process of producing cellulases in a host microbial cell using pretreated lignocellulosic material, i.e., pretreated corn stover. However, in the method, before using the pretreated corn stover or lignocellulosic biomass, the biomass was detoxified by different methods such as repeated soaking in water and washing, ion exchange, stripping, etc. this step is necessary because the host cell did not tolerate the inhibitors produced during the pretreatment.

Similarly, WO2011/133111A1 also used pretreated biomass to cultivate the cellulolytic *Trichoderma viride* NP13a for the enzyme production. But the pretreated materials were, filtered, washed with distilled water until the pretreated material had a pH of 7, and then dried. This additional step requires more water and additional money. Such detoxification is not feasible in the large-scale production of enzymes.

U.S. Pat. No. 10,526,593B2 discloses the use of a fungal strain *Penicillium funiculosum* NCIM 1228 to produce cellulases using Avicel, as pure cellulose, and wheat bran as carbon as well as inducer source. The total cellulolytic enzymes i.e., secretome was described in this invention. Composition of different enzymes were also mentioned. However, the document failed to describe the use of pretreated lignocellulosic biomass for the enzyme production; consequently, also does not describes the composition of enzymes produced using pretreated lignocellulosic biomass.

WO 2010/076552 A1 describes the production of cellulases enzymes by fermentation using fungal strain *Penicillium funiculosum* ATCC 11797. The substrates used for enzyme production were Avicel or carboxymethylcellulose or agricultural-forestry residue, in natural or pretreated. The enzyme produced by this fungal strain by using lignocellulosic biomass was much lower and difficult to use without concentration. As compared to our processes, this strain produces approximately 100 times lower cellulases (FPase). Other enzymes are also at very lower concentrations. Therefore, it is difficult to use such a process for commercial purpose.

WO2017174378A1 is related to the use of pretreated pomace for cellulolytic enzyme production. The pomace is the different lignocellulosic biomass as it contains very less (<5%) content of hemicelluloses/xylan. Other lignocellulosic biomass such as rice straw, wheat straw, sugarcane bagasse, cotton stalk, wood, etc contains 5-30% xylan/hemicelluloses content. Also, the described process did not produce any other valuable product simultaneously. Producing other valuable byproducts along with enzymes in a single step is always economically viable.

WO2017/177289 A1 relates to the process of enzyme production by *Trichoderma reesei* strains VTT-BR-00019 and biomass hydrolysis sequentially in a single reactor. In the enzyme production step pretreated biomass was not used directly but a biomass hydrolysate i.e. sugars or sugars from molasses or Avicel or lactose or both were used for enzyme production.

*Penicillium funiculosum* reported in the literature for the production of cellulases from pretreated lignocellulosic biomass or using pure cellulose in the cited documents (de Castro A M et al, DOI: 10.1007/s10295-009-0656-2; Choudhari V G et al, DOI:10.19080/AIBM.2017.04.555665; Maeda R N, et al, DOI: 10.1016/j.piotec.2012.10.014; Ogunyewo O A et al, DOI: 10.1016/j.procbio.2020.02.029; Lachke A H et al, Enzyme Microb. Technol., 1986, vol. 8; Randhawa A et al, DOI: 10.1186/s13068-018-1011-5; Ogunmolu F E et al, DOI: 10.1021/acs.jproteome.5b00542; Ogunmolu F E et al, DOI:10.1016/j.jprot.2018.03.025; Rao M et al, Biotechnology and Bioengineering, Vol. XXV, Pp. 1863-1871, 1983), but the titer of cellulase production is lower, and also no information was provided regarding the production of other valuable products/organic acids along with cellulases in a single step using the same microbial strain. Such a lower titer of the enzyme is not commercially feasible.

Liu et al (DOI:10.1007/s12010-014-0856-8) reported the direct conversion of pretreated straw cellulose using two different strains i.e., *Trichoderma reesei* for cellulase production and *Yarrowia lipolytica* SWJ-1b for citric acid production from hydrolyzed sugars in one reactor. Li et al (DOI:1 0.1016/j.ymben.2019.05.007) described the construction of *Myceliophthora thermophila* strain, through metabolic engineering into a platform that can directly convert lignocellulose material into malic and succinic acid. The constructed strain also produces cellulases along with malic and succinic acid. Here also the enzyme titer protein concentration is lower and such strains couldn't be used commercially for both cellulases as well as acid production in a single step.

Weiliang Hou and Jie Bao (DOI: 10.1016/j.biortech.2018.01.011) described the production of citric acid from cellulose but not directly. The cellulose first hydrolyzed using commercial cellulase preparation and the hydrolyzed sugar used to produce citric acid in a different reactor by *Aspergillus niger*. Scholz S A et al (DOI:10.1002/bit.26509) used synthetic fungal consortia composed of *Trichoderma reesei* and *Rhizopus delemar* for cellulase and fumaric acid production respectively, from microcrystalline cellulose (MCC) and alkaline pretreated corn stover.

EP3628751A1 discloses hyper-cellulolytic, catabolite derepressed mutant of ascomycetes fungus, *Penicillium funiculosum* NCIM 1228 strain. The document also describes mutant fungal strain of *Penicillium funiculosum* MRJ-16 with hyper-cellulolytic and catabolite derepressed activity, having ability to produce enzymes in the presence of catabolite repressor such as D-glucose.

Although, available literature provides several methods for production of cellulases enzymes and citric acid, however, the available methods face several challenges. Thus, there is a need in the art to develop a process for simultaneous production of cellulolytic enzymes and citric acid in a single step. The production of commodity chemicals such as citric acid, lactic acid, adipic acid, itaconic acid, etc. along with high titer of cellulolytic enzymes using lignocellulosic material could help to reduce the cost of enzyme and overall biorefinery process. Further, the production of these chemicals along with enzyme by a single microbial species in a single step will further improve the feasibility of commercialization.

Furthermore, the main Indian Patent Application No. 201821044919 disclosed a process for production of cellulases enzymes by *Penicillium funiculosum*. The method aimed at providing a method to produce cellulases enzymes in batch process using low-cost media components in specific quantities along with *Penicillium funiculosum* mutant strain, which in turn increased the commercial viability of the process. However, the present invention discloses a process for simultaneous production of high titer cellulolytic enzymes along with citric acid in batch/fed process which has several advantages over the main Indian Patent Application No. 201821044919 as described below.

- Direct and simultaneous production of cellulolytic and hemicellulolytic enzymes and citric acid from cellulose or lignocellulosic biomass.
- Production of citric acid along with cellulolytic enzyme is in single step and using single microbial strain *Penicillium funiculosum* MRJ-16.
- The present invention utilizes modified production/fermentation media to increase the enzyme production (glycerol replaced by glucose; added new component i.e., copper sulfate in media).
- Designed a fed-batch process to increase the enzyme production from 6.5 FPU/ml to 11.2 FPU/ml (as compared to previous patent).
- The produced cellulolytic enzyme cocktail does not require any external enzyme supplementation for hydrolysis of acid pretreated lignocellulosic biomass.
- Direct use of produced enzymes along with mycelia and biomass residues is possible without any downstream processing.

After production, if separated, mycelia and biomass residues (mostly lignin) is used as enzyme source for hydrolysis of pretreated biomass.

Enzyme mixture has an appropriate mix of necessary enzymes which can be used for the hydrolysis of pretreated lignocellulosic biomass to make the 2G ethanol process economically viable.

SUMMARY OF THE INVENTION

In an aspect of the present invention, there is provided a process for simultaneous production of citric acid and cellulolytic enzymes, the process comprising:
(i) adding slurry of a pre-treated lignocellulosic biomass or cellulose in a fermentation media;
(ii) inoculating 10% (v/v) active liquid seed culture of Penicillium funiculosum MRJ-16 with Accession No. MTCC-25142, and date of deposition as 12 Jun. 2017, deposited at IMTECH in the fermentation media of step (i);
(iii) subjecting the culture of step (ii) to fermentation in an aerated fermenter at a temperature of 28-33° C. for a duration of 96 hours;
(iv) collecting enzyme broth after fermentation of step (iii) to obtain citric acid and cellulolytic enzymes.

In an embodiment of the present invention, there is provided a process wherein the lignocellulosic biomass is selected from the group consisting of rice straw, wheat straw and sugarcane bagasse.

In another embodiment of the present invention, there is provided a process wherein the fermentation media comprises ammonium sulfate, $KH_2PO_4$, $MgSO_4 \cdot 7H_2O$, $CaCO_3$, glucose, copper sulfate, corn steep liquor, and Tween-80.

In yet another embodiment of the present invention, there is provided a process wherein the pretreatment comprises treating the biomass with 0.5-1.5% w/w of sulfuric acid at a temperature of 110-160° C. for 10-30 minutes.

In still another embodiment of the present invention, there is provided a process wherein the pretreatment of biomass slurry additionally comprises adjusting pH of the slurry to 5.0-5.5 with a pH adjuster.

In yet another embodiment of the present invention, there is provided a process wherein the pre-treated biomass slurry is subjected to fermentation without any detoxification.

In an embodiment of the present invention, there is provided a process wherein the pretreated biomass, without detoxification is used in the range of 2-8%.

In another embodiment of the present invention, there is provided a process wherein during the fermentation, dissolved oxygen is maintained at 20% using agitation and aeration.

In still another embodiment of the present invention, there is provided a process, wherein the obtained enzyme broth comprises enzymes selected from FPase, CMCase, cellobiohydrolase, Cellobiase/β-glucosidase, α-L arabinofuranosidase, endo/exo xylanases, β-xylosidase, oxidases, or a mixture thereof.

In yet another embodiment of the present invention, there is provided a process, wherein the obtained enzyme broth is further used for hydrolysis of pretreated lignocellulosic biomass.

In another aspect of the invention, there is provided a fed-batch process for simultaneous production of citric acid and cellulolytic enzymes, the process comprising:
(i) adding slurry of a pre-treated lignocellulosic biomass at a concentration of 6% (dry weight basis) or cellulose at concentration of 3.3% in a fermentation media;
(ii) inoculating 10% (v/v) active liquid seed culture of Penicillium funiculosum MRJ-16 in the fermentation media of step (i);
(iii) subjecting the culture of step (ii) to fermentation in an aerated fermenter at a temperature of 28-33° C.;
(iv) adding media in 2×/double concentration after duration of 48-60 hours; and
(v) collecting enzyme broth after a duration of 96 hours to obtain citric acid and cellulolytic enzymes.

In an embodiment of the present invention, there is provided a fed-batch process wherein the fermentation media is fed in the fermenter after interval of every 8-12 hours.

In another embodiment of the present invention, there is provided a fed-batch process for simultaneous production of citric acid and cellulolytic enzymes, wherein the fed-batch process is designed to increase the enzyme production.

These and other features, aspects, and advantages of the present subject matter will be better understood with reference to the following description. This summary is provided to introduce a selection of concepts in a simplified form.

BRIEF DESCRIPTION OF DRAWINGS

These and other features, aspects, and advantages of the present invention will become better understood when the following detailed description is read with reference to the accompanying drawings in which like characters represent like parts throughout the drawings wherein:

FIG. 1 illustrates a flow diagram depicting the process for simultaneous production of citric acid and cellulolytic enzymes from a lignocellulosic biomass.

DETAILED DESCRIPTION OF THE INVENTION

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

Definition

For the purposes of this invention, the following terms will have the meaning as specified therein:

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

"Pre-treated biomass" or "Pretreatment of biomass" used herein clears away physical and chemical barriers that make native biomass recalcitrant and exposes cellulose for better enzymatic hydrolysis. In most of the pretreatment, chemical (acid or alkali) and physical (high temperature or pressure) parameters are used individually or in mixed manner to remove barriers for enzymatic hydrolysis and improve the enzymatic digestibility.

"Detoxification" used herein is the process where the inhibitors (toxic compound such hydroxymethyl furfural, furfural, acetic acids, formic acids, etc.) produced during the pretreatment process are removed or neutralized from pre-treated biomass by chemical, physical, or biological process.

"Cellulase enzyme" used herein is a mixed form of enzyme which is mostly composed of exo hydrolase, endo-hydrolase and beta-glucosidase and other auxiliary enzymes. Cellulase breaks down the cellulose molecule into mono-saccharide and shorter polysaccharides or oligosaccharides.

The present invention relates to a batch process for simultaneous production of high titer cellulolytic enzymes and citric acid using lignocellulosic biomass or cellulose. The process utilizes a single microbial strain i.e., *Penicillium funiculosum* MRJ-16 mutant, using designed fermentation media and cellulosic substrate or pretreated lignocellulosic biomass, without detoxification, as carbon and/or enzyme-inducer source. Initially, the strain *Penicillium funiculosum* MRJ-16 is grown in a stirred reactor under aerobic conditions containing fermentation media components comprising (per L: ammonium sulfate 5 g, $KH_2PO4$ 6 g, $MgSO_4 \cdot 7H_2O$ 1 g, $CaCO_3$ 5 g, Glucose 2.5 g, Copper sulfate 0.1 g, Corn steep liquor 30 g, and Tween-80 2 mL) and one of the carbon source such as pure cellulose or pretreated lignocellulosic biomass e.g., rice straw, wheat straw, sugarcane bagasse, etc. After 4-5 days of reactor run, the broth was analyzed for different enzymes and citric acid production. The present process can be performed in a batch mode wherein the pretreated biomass, without detoxification, was used at 2-8% (most preferred 6%). If cellulose was used, then the concentration in batch mode was 3-5%. Airflow was maintained in between 0.5-1 VVM, and the temperature was maintained in between 28-33° C. Further, during the process the dissolved oxygen was maintained above 20% of saturation and pH was maintained between 4.0-5.5. The batch run was completed within the duration of 96 hours. The enzyme preparation obtained after the process comprises a mixture of the enzyme such as FPase, CMCase, cellobiohydrolase, cellobiase/β-glucosidase, α-L arabino-furanosidase, endo/exo xylanases, β-xylosidase, oxidases, or mixture thereof. The produced enzyme broth can used for hydrolysis of pretreated lignocellulosic biomass for mono-meric sugar production, and accordingly the broth may undergo solid-liquid separation by centrifugation or through a filter press. The separated solids which are of mycelia and unused biomass residues i.e., lignin is used as an enzyme source for the hydrolysis of pretreated lignocellulosic biomass. The clarified broth free from any solid is concentrated through ultrafiltration using a 5 or 10 KD membrane. Further, the concentrated broth is used as a cellulolytic enzyme source for the hydrolysis of pretreated lignocellulosic biomass. The filtrate received from ultrafiltration used as a citric acid source for further purification and their use.

The present invention utilizes a single microbial strain i.e., *Penicillium funiculosum* MRJ-16 mutant. The strain is having Accession No. MTCC-25142 and was deposited at IMTECH, Chandigarh on $12^{th}$ Jun. 2017.

Thus, in accordance with the present invention, there is provided a process for simultaneous production of citric acid and cellulolytic enzymes, the process comprising:

(i) adding slurry of a pre-treated lignocellulosic biomass or cellulose in a fermentation media;
(ii) inoculating 10% (v/v) active liquid seed culture of *Penicillium funiculosum* MRJ-16 in the fermentation media of step (i);
(iii) subjecting the culture of step (ii) to fermentation in an aerated fermenter at a temperature of 28-33° C. for a duration of 96 hours;
(iv) collecting enzyme broth after fermentation of step (iii) to obtain citric acid and cellulolytic enzymes.

In an embodiment of the present invention, there is provided a process for simultaneous production of citric acid and cellulolytic enzymes, wherein the lignocellulosic biomass is selected from the group consisting of rice straw, wheat straw and sugarcane bagasse.

In another embodiment of the present invention, there is provided a process for simultaneous production of citric acid and cellulolytic enzymes, wherein the fermentation media comprises ammonium sulfate, $KH_2PO4$, $MgSO_4 \cdot 7H_2O$, $CaCO_3$, Glucose, Copper sulfate, corn steep liquor, and Tween-80. The process of the present invention utilizes the fermentation media which is designed for high titter cellulolytic enzyme production. The present inventors have specifically designed the fermentation media to increase the enzyme production. The fermentation media used in the present invention comprises per litre: ammonium sulfate 5 g, $KH_2PO_4$ 6 g, $MgSO_4 \cdot 7H_2O$ 1 g, $CaCO_3$ 5 g, Glucose 2.5 g, Copper sulfate 0.1 g, Corn steep liquor 30 g, and Tween-80 2 mL).

In an embodiment of the present invention, there is provided a process for simultaneous production of citric acid and cellulolytic enzymes, wherein the pretreatment comprises treating the biomass with 0.5-1.5% w/w of sulfuric acid at a temperature of 110-160° C. for 10-30 minutes.

In another embodiment of the present invention, there is provided a process for simultaneous production of citric acid and cellulolytic enzymes, wherein the pretreatment of biomass slurry additionally comprises adjusting pH of the slurry to 5.0-5.5 with a pH adjuster.

In an embodiment of the present invention, there is provided a process for simultaneous production of citric acid and cellulolytic enzymes, wherein the pre-treated biomass slurry is subjected to fermentation without any detoxification.

In another embodiment of the present invention, there is provided a process for simultaneous production of citric acid and cellulolytic enzymes, wherein the pretreated biomass, without detoxification is used in the range of 2-8%.

In an embodiment of the present invention, there is provided a process for simultaneous production of citric acid and cellulolytic enzymes, wherein during the fermentation, dissolved oxygen is maintained at 20% using agitation and aeration.

In another embodiment of the present invention, there is provided a process for simultaneous production of citric acid and cellulolytic enzymes, wherein the obtained enzyme broth comprises enzymes selected from FPase, CMCase, cellobiohydrolase, Cellobiase/β-glucosidase, α-L arabino-furanosidase, endo/exo xylanases, β-xylosidase, oxidases, or a mixture thereof.

In an embodiment of the present invention, there is provided a process for simultaneous production of citric acid and cellulolytic enzymes, wherein the obtained enzyme broth is further used for hydrolysis of pretreated lignocellulosic biomass.

In another aspect of the present invention, there is provided a fed-batch process for simultaneous production of citric acid and cellulolytic enzymes. The fed-batch process is designed to increase enzyme production in which pre-treated biomass slurry concentration as a carbon source was used at 6% (dry weight basis) concentration or cellulose was used at a concentration of 3.3%. The process was carried out as per batch process and after 48-60 hours of growth in the stirred reactor, fermentation media in double strength (per L: cellulose 66 g or pretreated biomass slurry 120 g, Ammonium sulfate 10 g, $KH_2PO_4$ 12 g, $MgSO_4 \cdot 7H_2O$ 2 g, $CaCO_3$ 10 g, Corn steep liquor 56 g, and Tween-80 4 mL) was added. Further, the fermentation media was fed after an interval of every 12 hours. For 4 liter starting broth volume, 0.25 litres of double strength feeding media was used to feed the reactor for every 8-12 hours. Thus, total 1 litre double strength feed/fermentation media was added for 4 litres initial broth volume. The fed-batch run was completed in 96 hours as indicated in Example 4.

Thus, in accordance with another aspect of the present invention, there is provided a fed-batch process for simultaneous production of citric acid and cellulolytic enzymes, the process comprising:
(i) adding slurry of a pre-treated lignocellulosic biomass at a concentration of 6% (dry weight basis) or cellulose at concentration of 3.3% in a fermentation media;
(ii) inoculating 10% (v/v) active liquid seed culture of *Penicillium funiculosum* MRJ-16 in the fermentation media of step (i);
(iii) subjecting the culture of step (ii) to fermentation in an aerated fermenter at a temperature of 28-33° C.;
(iv) adding media in 2×/double concentration after duration of 48-60 hours; and
(v) collecting enzyme broth after a duration of 96 hours to obtain citric acid and cellulolytic enzymes.

In an embodiment of the present invention, there is provided a fed-batch process for simultaneous production of citric acid and cellulolytic enzymes, wherein the fermentation media is fed in the fermenter after interval of every 8-12 hours.

In another embodiment of the present invention, there is provided a fed-batch process for simultaneous production of citric acid and cellulolytic enzymes, wherein the fed-batch process is designed to increase the enzyme production.

The present invention relates to a simultaneous production of citric acid from cellulosic material (pure cellulose or pretreated lignocellulosic biomass) along with high titer production of cellulolytic enzymes. Particularly, in the process of the present invention, high titer cellulolytic enzymes are produced along with citric acid directly from cellulose or lignocellulosic material in a single step and using single microbial strain. The present invention also provides a production media for high titer cellulolytic enzyme production. Diverse enzymes (cellulases and hemicellulases) are produced such as endoglucanases, cellobiohydrolases, β-glucosidases, endoxylanases, β-xylosidases, α-L-arabino-furanosidases, etc. The fermentation can also be performed by a fed-batch process for further improvement of the enzyme titer. The produced cellulolytic enzyme cocktail does not require any additional/external enzymes for hydrolysis of acid pretreated lignocellulosic biomass and is sufficient for efficient hydrolysis of pretreated biomass. Further, in the process of the present invention, detoxification of pretreated biomass is not required for enzyme production, which reduces the step of washing requiring lot of water. In addition, after production, if separated, mycelia and biomass residues (mostly lignin) is used as enzyme source for hydrolysis of pretreated biomass. Moreover, the process of the present invention results in high titer production of citric acid without any additional process modification or any addition of media component, which eventually reduces the overall cost of industrial biorefinery processes.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Production of Cellulolytic Enzymes Using Pre-Treated Biomass or Cellulose as Carbon Source (Main Indian Patent Application No. 201821044919)

For the production of cellulolytic enzymes, the fermentation process was carried out in an aerated stirred tank bioreactor of 7 L glass jacketed vessel with 5 L working volume. Initially, the acid pretreated lignocellulosic biomass such as sugarcane bagasse/rice straw/wheat straw or cellulose in 1:1 or 1:2 ratio was used as carbon source. The pretreatment of biomass was done at 0.5-1.5% w/w sulfuric acid concentration at a temperature of 110-160° C. for 10-30 minutes. The fermentation media components of fermentation media used were 5 g/L ammonium sulphate, 6 g/L $KH_2PO_4$, 1 g/L $MgSO_4 \cdot 7H_2O$, 5 g/L $CaCO_3$, 2.5 g/L glycerol, 30 g/L corn steep solids, 30 g/L cellulose and 2 ml/L Tween-80. The fermenter containing 4.5 L medium was sterilized at 120° C. for 20 minutes. After cooling, the temperature was kept at 30° C. and the pH adjusted to 5.5, aeration above 50% followed by inoculation with 10% active liquid seed of *Penicillium funiculosum* MRJ-16 mutant w. The pH during entire fermentation process was not regulated and no nutrients were added; only aeration was maintained above 30%. After 96 hours, the enzyme broth was collected, centrifuged and analysis of clear enzyme broth was done. The results obtained were 17.6 g/L of protein, 72 IU/ml of β-glucosidase and 6.5 FPU/ml of filter paper activity.

Example 2: Simultaneous Cellulolytic/Xylanolytic and Citric Acid Production Using Acid Pretreated Rice Straw Slurry An in-house mutant strain *Penicillium funiculosum* MRJ-16 was used for enzyme and citric acid production. Initially, the whole slurry of lignocellulosic biomass such as Rice straw biomass obtained after dilute-sulfuric acid pretreatment was used as a carbon source at total solid loading 6% (w/v). Pretreatment to rice straw was done at 0.5-1.5% w/w sulfuric acid concentration, at the temperature 110-160° C. for 10-30 minutes. The enzyme production process was performed in a 7 L stirred tank aerobic reactor with 4 L working volume. The composition of the production/fermentation media used was (per L): ammonium sulfate 5 g, $KH_2PO_4$ 6 g, $MgSO_4 \cdot 7H_2O$ 1 g, $CaCO_3$ 5 g, Glucose 2.5 g, Copper sulfate 0.1 g, Corn steep liquor 27 g, and Tween-80 2 mL. The 7 L reactor containing 4 L above media and 6% pretreated rice straw were sterilized at 120° C. for 20-30 minutes. Before inoculation, the reactor was allowed to cool up to 30° C. and the medium pH was adjusted to 5.5. Further, the experimental set was inoculated with 10% (v/v) active liquid seed culture of the mutant strain MRJ-16, prepared in similar media in shake flask using spore stock stored at −80° C. During the entire stirred tank aerobic fermentation run, no pH adjustment and nutrient supplementation was carried out. Dissolved oxygen was maintained above 20% using agitation and aeration. Temperature was maintained around 30° C. throughout the run. After 96 hours of the run, the enzyme broth was collected, centrifuged (if required) and analysis of enzyme activities and citric acid was performed. It was reported that the mutant strain produced 11.21 g/L citric acid. The results of secretome analysis obtained were 5.9 FPU/mL of filter paper activity, 65 IU/mL of β-glucosidase activity, 2.1 IU/mL of β-xylosidase activity, 0.41 IU/mL of α-L arabinofuranosidase activity, 219 IU/mL of xylanase activity, and 76 IU/mL of endoglucanase (CMcase) activity. The analysis of enzyme broth for citric acid (Li et al; 2019, DOI: 10.1016/j.ymben.2019.05.007) and above-mentioned enzyme activities in the present invention may be done according to the known methods available in the literature [Ghose, T. K., 1987; Measurement of cellulase activities; Pure Appl. Chem. 59, 257-268].

Example 3: Simultaneous Cellulolytic/Xylanolytic and Citric Acid Production Using Cellulose as Carbon Source Cultivation of *Penicillium funiculosum* MRJ-16 mutant strain was conducted under conditions and media composition identical to example no. 1 except that 3.3% (w/v) cellulose was used as a carbon source instead of 6% pretreated rice straw slurry. As mentioned above, the enzyme broth collected after 96 hours of fermentation was assayed. Analytical determination of enzyme broth resulted in 7.96 FPU/mL, 82.19 IU/mL of β-glucosidase activity, 2.51 IU/mL of β-xylosidase activity, 0.55 IU/mL of α-L arabinofuranosidase activity, 190 IU/mL of xylanase activity, and 125 IU/mL of endoglucanase (CMCase) activity. The results demonstrated that the mutant strain produced 14.60 g/L citric acid from cellulose.

Example 4: Fed-Batch Process to Increase Enzyme Production

The fed-batch process of enzyme and citric acid production was carried out in 7 L stirred tank aerobic reactor. Strain *Penicillium funiculosum* MRJ-16 was grown initially in 4 L production media using rice straw slurry (6%) or cellulose (3.3%) same as example 1. After 48-60 hrs of the run, the fed-batch process started. The feed media composition was (per L): cellulose 66 g or pretreated biomass slurry 120 g, Ammonium sulfate 10 g, $KH_2PO_4$ 12 g, $MgSO_4 \cdot 7H_2O$ 2 g, $CaCO_3$ 10 g, Copper sulfate 0.1 g, Corn steep liquor 56 g, and Tween-80 4 ml. 250 mL of this feed-media was transferred into the reactor after 48-60 h of initial reactor run. Such feeding was done every 8-12 h interval. Total 1 L feed media was added. During the entire stirred tank aerobic fermentation run no pH adjustment was carried out. Dissolved oxygen maintained above 20% using agitation and aeration. Fed-batch run was stopped at 96 h or continued further as per requirement. After 96 h of the run, the enzyme broth was collected, centrifuged (if required) and analysis of enzyme activities and citric acid was performed. If cellulose used as a carbon source, the mutant strain produced 16 g/L citric acid. The results of secretome analysis obtained were 11.2 FPU/mL of filter paper activity, 108 IU/mL of β-glucosidase activity, 2.8 IU/mL of β-xylosidase activity, 0.75 IU/mL of α-L arabinofuranosidase activity, 209 IU/mL of xylanase activity, and 137 IU/mL of endoglucanase (CMcase) activity.

Example 5: Performing Hydrolysis of Whole Slurry of Pretreated Lignocellulosic Biomass (Rice Straw)

In order to determine the efficiency of the enzyme cocktail produced in Example no. 1 or 2 to hydrolyze whole slurry of the dilute-acid pretreated lignocellulosic biomass such as rice straw and for the production of sugars, the enzyme was first separated from fungal mycelia by centrifugation or whole broth along with fungal mycelia was used as such for hydrolysis. Subsequently, hydrolysis was performed at high substrate loading of biomass i.e., 15% (w/v) at pH 4-5, temperature 50° C., and enzyme loadings of 2-5 FPU/g of dry biomass. The sugars which were produced after the hydrolysis were determined by HPLC method. It was found that the enzyme cocktail worked efficiently and lead to a 60-80% glucan conversion within the duration of 48 hours.

Example 6: Performing Hydrolysis of Pretreated Rice Straw Using Solid Residues Left in the Enzyme Production Process After the enzyme and citric acid production were completed as per example 1 or 2 or 3, the obtained enzyme broth was separated to remove the mycelia and/or unutilized rice straw residues (e.g. lignin) for further downstream processing (enzyme concentration through ultrafiltration). The hydrolysis of the dilute-acid pretreated lignocellulosic biomass such as rice straw was conducted at 15% solid loading. The left-over solid residue at 0.25-1 g/g of rice straw slurry was used as an enzyme source. Further, the hydrolysis was performed at high substrate loading of biomass i.e. 15% (w/v) at pH 4-5, temperature 50° C. with proper mixing. The sugars which were released were determined by HPLC method. It was observed that within the duration of 48 hours, 50-70% of glucan conversion took place.

The invention claimed is:
1. A process for simultaneous production of citric acid and cellulolytic enzymes, the process comprising:
   (i) adding slurry of a pre-treated lignocellulosic biomass or cellulose in a fermentation media;
   (ii) inoculating 10% (v/v) active liquid seed culture of *Penicillium funiculosum* MRJ-16 (MTCC-25142) in the fermentation media of step (i);
   (iii) subjecting the culture of step (ii) to fermentation in an aerated fermenter at a temperature of 28-33° C. for a duration of 96 hours; and
   (iv) collecting enzyme broth after fermentation of step (iii) to obtain citric acid and cellulolytic enzymes.
2. The process as claimed in claim 1, wherein the lignocellulosic biomass is selected from the group consisting of rice straw, wheat straw and sugarcane bagasse.
3. The process as claimed in claim 1, wherein the fermentation media comprises ammonium sulfate, $KH_2PO_4$, $MgSO_4 \cdot 7H_2O$, $CaCO_3$, glucose, copper sulfate, corn steep liquor, and Tween-80.

4. The process as claimed in claim 1, wherein the pretreatment comprises treating the biomass with 0.5-1.5% w/w of sulfuric acid at a temperature of 110-160° C. for 10-30 minutes.

5. The process as claimed in claim 4, wherein the pretreatment of biomass slurry additionally comprises adjusting pH of the slurry to 5.0-5.5 with a pH adjuster.

6. The process as claimed in claim 1, wherein the pretreated biomass slurry is subjected to fermentation without any detoxification.

7. The process as claimed in claim 6, wherein the pretreated biomass, without detoxification is used in the range of 2-8%.

8. The process as claimed in claim 1, wherein during the fermentation, dissolved oxygen is maintained at 20% using agitation and aeration.

9. The process as claimed in claim 1, wherein the obtained enzyme broth comprises enzymes selected from FPase, CMCase, cellobiohydrolase, Cellobiase/β-glucosidase, α-L arabinofuranosidase, endo/exo xylanases, β-xylosidase, oxidases, or a mixture thereof.

10. The process as claimed in claim 1, wherein the obtained enzyme broth is further used for hydrolysis of pretreated lignocellulosic biomass.

11. A fed-batch process for simultaneous production of citric acid and cellulolytic enzymes, the process comprising:
(i) adding slurry of a pre-treated lignocellulosic biomass at a concentration of 6% (dry weight basis) or cellulose at concentration of 3.3% in a fermentation media;
(ii) inoculating 10% (v/v) active liquid seed culture of *Penicillium funiculosum* MRJ-16 in the fermentation media of step (i);
(iii) subjecting the culture of step (ii) to fermentation in an aerated fermenter at a temperature of 28-33° C.;
(iv) adding media in 2×/double concentration after duration of 48-60 hours; and
(v) collecting enzyme broth after a duration of 96 hours to obtain citric acid and cellulolytic enzymes.

12. The process as claimed in claim 11, wherein the fermentation media is fed in the fermenter after interval of every 8-12 hours.

* * * * *